US010923221B1

(12) United States Patent
Mann et al.

(10) Patent No.: US 10,923,221 B1
(45) Date of Patent: Feb. 16, 2021

(54) SYSTEM AND METHOD FOR ADMINISTERING MEDICATIONS

(71) Applicant: ALLSCRIPTS SOFTWARE, LLC, Chicago, IL (US)

(72) Inventors: Carin Lee Mann, Raleigh, NC (US); Anthony Edward Stuart, Wake Forest, NC (US); Mary Sumner Johnson, Raleigh, NC (US); Leigh Randal McClure, Raleigh, NC (US); Christy Jill Reed, Raleigh, NC (US)

(73) Assignee: Allscripts Software, LLC, Chicago, IL (US)

( * ) Notice: Subject to any disclaimer, the term of this patent is extended or adjusted under 35 U.S.C. 154(b) by 656 days.

(21) Appl. No.: 15/859,646

(22) Filed: Dec. 31, 2017

Related U.S. Application Data

(63) Continuation of application No. 14/556,218, filed on Nov. 30, 2014, now abandoned, which is a continuation-in-part of application No. 14/556,193, filed on Nov. 30, 2014, now abandoned.

(60) Provisional application No. 62/036,556, filed on Aug. 12, 2014, provisional application No. 62/036,137, filed on Aug. 12, 2014.

(51) Int. Cl.
*G16H 20/10* (2018.01)
*G16H 80/00* (2018.01)

(52) U.S. Cl.
CPC ............. *G16H 20/10* (2018.01); *G16H 80/00* (2018.01)

(58) Field of Classification Search
USPC ........................................................ 705/2, 3
See application file for complete search history.

(56) References Cited

U.S. PATENT DOCUMENTS

| 4,857,713 | A | 8/1989 | Brown | |
|---|---|---|---|---|
| 7,155,306 | B2 | 12/2006 | Haitin | |
| 8,311,854 | B1 * | 11/2012 | Stanley | G16H 10/60 705/3 |
| 8,666,774 | B1 * | 3/2014 | Gonzales, Jr. | G16H 40/20 705/2 |

(Continued)

OTHER PUBLICATIONS

Vista Bar Code Medication Administration (BCMA) GUI User Manual, Department of Veterans Affairs, Office of Enterprise Development, Version 3.0, Feb. 2004 (Reissued Jan. 2009) (Year: 2009).*

(Continued)

*Primary Examiner* — Aryan E Weisenfeld
*Assistant Examiner* — Joshua B Blanchette
(74) *Attorney, Agent, or Firm* — Loza & Loza LLP; Peter Zura

(57) ABSTRACT

A computer readable medium storing a computer program for providing a medication administration workflow in a user-interface (UI). The computer program executable by at least one processor, the computer program comprising sets of instructions for receiving one or more scanned medications for administration to a selected patient, determining a status of each of the one or more scanned medications, displaying a medication list including at least the one or more scanned medications and the respective status of the scanned medication, selecting one of the one or more medications in the medication list, and addressing any outstanding items associated with the selected medication.

13 Claims, 24 Drawing Sheets

(56) References Cited

U.S. PATENT DOCUMENTS

| | | | |
|---|---|---|---|
| 2005/0004700 A1* | 1/2005 | DiMaggio | G06F 19/3462 |
| | | | 700/213 |
| 2006/0136167 A1 | 6/2006 | Nye | |
| 2007/0005396 A1 | 1/2007 | Lee | |
| 2007/0136237 A1* | 6/2007 | Barker | G06F 21/6227 |
| 2007/0192143 A1* | 8/2007 | Krishnan | G06Q 50/22 |
| | | | 705/3 |
| 2007/0233521 A1 | 10/2007 | Wehba | |
| 2008/0154642 A1* | 6/2008 | Marble | G16H 15/00 |
| | | | 705/3 |
| 2011/0010195 A1* | 1/2011 | Cohn | G06Q 50/24 |
| | | | 705/3 |
| 2011/0246224 A1* | 10/2011 | Green | G06Q 50/24 |
| | | | 705/2 |
| 2012/0130197 A1* | 5/2012 | Kugler | G16H 40/67 |
| | | | 600/300 |
| 2012/0166220 A1* | 6/2012 | Baldwin | G06Q 50/24 |
| | | | 705/3 |
| 2012/0173258 A1* | 7/2012 | Hofmann | G06Q 50/22 |
| | | | 705/2 |
| 2012/0173277 A1* | 7/2012 | Yates | G06Q 50/24 |
| | | | 705/3 |
| 2012/0323602 A1 | 12/2012 | Ryan | |

OTHER PUBLICATIONS

Information Disclosure Statement (IDS) Letter Regarding Common Patent Application(s), dated Feb. 6, 2018.
Yongxing Deng, Vincent Siao, Josh Smith & Stephanie Hornung; Asana Blog, Aug. 27, 2013, retrieved Sep. 7, 2017 from https://blog.asana.com/2013/08/mergetaske/ (Year: 2013).

* cited by examiner

SYSTEM AND METHOD FOR ADMINISTERING MEDICATIONS

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention relates to computing devices. More specifically, the present invention relates to administering medications.

Due to managing multiple patients and multiple issues at one time, nurses have become expert at multi-tasking. Anytime a nurse enters a room he/she will perform more than one task and ensure their patients have what they need. Additionally, nurses are often interrupted while they are performing their work. To ensure everything has been completed, most, if not all, nurses will have a piece of paper in their pocket to track things down throughout the day.

Unfortunately, most Electronic Health Records (EHRs) do not support this type of multi-tasking workflow, particularly with medication administration. When administering medications, current systems require nurses to go through every step for each medication before moving to the next medication. This requirement decreases a nurse's efficiency because he/she has to stop the scanning process to complete multiple screens. Also, this requirement may be a bigger problem if the nurse is interrupted during the scanning process since there is no indication in current systems regarding what medication has been scanned already and where he/she may be in the process with a certain medication.

Therefore, there exists a need for an improved method and system for administering medications. This and other needs are addressed by one or more aspects of the present invention.

SUMMARY OF THE INVENTION

The present invention includes many aspects and features. Moreover, while many aspects and features relate to, and are described in, the context of healthcare applications, the present invention is not limited to use only in this context, as will become apparent from the following summaries and detailed descriptions of aspects, features, and one or more embodiments of the present invention.

Accordingly, one aspect of the present invention relates to a computer readable medium storing a computer program for providing a medication administration workflow in a user-interface (UI). The computer program executable by at least one processor, the computer program comprising sets of instructions for receiving one or more scanned medications for administration to a selected patient, determining a status of each of the one or more scanned medications, displaying a medication list including at least the one or more scanned medications and the respective status of the scanned medication, selecting one of the one or more medications in the medication list, and addressing any outstanding items associated with the selected medication.

In a feature of this aspect, the one or more scanned medications in the medication list are scanned in one after the other.

In another feature of this aspect, the outstanding items associated with each of the one or more scanned medications are addressed after all of the one or more medications in the medication list are scanned in.

In another feature of this aspect, the computer program further comprises instructions for updating the status for each medication in the scanned medication list as the one or more outstanding items associated with the respective one or more scanned medications is addressed.

In another feature of this aspect, the one or more outstanding items associated with one of the one or more scanned medications is addressed prior to scanning in another medication.

In another feature of this aspect, all outstanding items for each of the one or more scanned medications are addressed prior to completing the administration of the medications in the medication list.

Another aspect of the present invention relates to a computing device comprising one or more processors, and a computer readable medium storing a computer program for providing a medication administration workflow in a user-interface (UI). The computer program executable by at least one of the one or more processors, the computer program comprising sets of instructions for receiving one or more scanned medications for administration to a selected patient, determining a status of each of the one or more scanned medications, displaying a medication list including at least the one or more scanned medications and the respective status of the scanned medication, selecting one of the one or more medications in the medication list, and addressing any outstanding items associated with the selected medication.

In a feature of this aspect, the one or more scanned medications in the medication list are scanned in one after the other.

In another feature of this aspect, the outstanding items associated with each of the one or more scanned medications are addressed after all of the one or more medications in the medication list are scanned in.

In another feature of this aspect, the computer program further comprises instructions for updating the status for each medication in the scanned medication list as the one or more outstanding items associated with the respective one or more scanned medications is addressed.

In another feature of this aspect, the one or more outstanding items associated with one of the one or more scanned medications is addressed prior to scanning in another medication.

In another feature of this aspect, all outstanding items for each of the one or more scanned medications are addressed prior to completing the administration of the medications in the medication list.

Another aspect of the present invention relates to a method for providing a medication administration workflow in a user-interface (UI) comprising receiving one or more scanned medications for administration to a selected patient, determining a status of each of the one or more scanned medications, displaying a medication list including at least the one or more scanned medications and the respective status of the scanned medication, selecting one of the one or more medications in the medication list, and addressing any outstanding items associated with the selected medication.

In a feature of this aspect, the one or more scanned medications in the medication list are scanned in one after the other.

In another feature of this aspect, the outstanding items associated with each of the one or more scanned medications are addressed after all of the one or more medications in the medication list are scanned in.

In another feature of this aspect, the computer program further comprises instructions for updating the status for each medication in the scanned medication list as the one or more outstanding items associated with the respective one or more scanned medications is addressed.

In another feature of this aspect, the one or more outstanding items associated with one of the one or more scanned medications is addressed prior to scanning in another medication.

In another feature of this aspect, all outstanding items for each of the one or more scanned medications are addressed prior to completing the administration of the medications in the medication list.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

FIG. 5 is an example screenshot of a full screen of the Medication/Dose section of FIG. 4;

FIG. 19 is an example screenshot of the Med Admin UI wherein the Status Box includes a Status message;

FIG. 21 is an example screenshot of a Task Screen;

FIG. 22 is an example screenshot of a Medication Summary in accordance with a disclosed implementation of the present invention;

DETAILED DESCRIPTION

Figure 1:
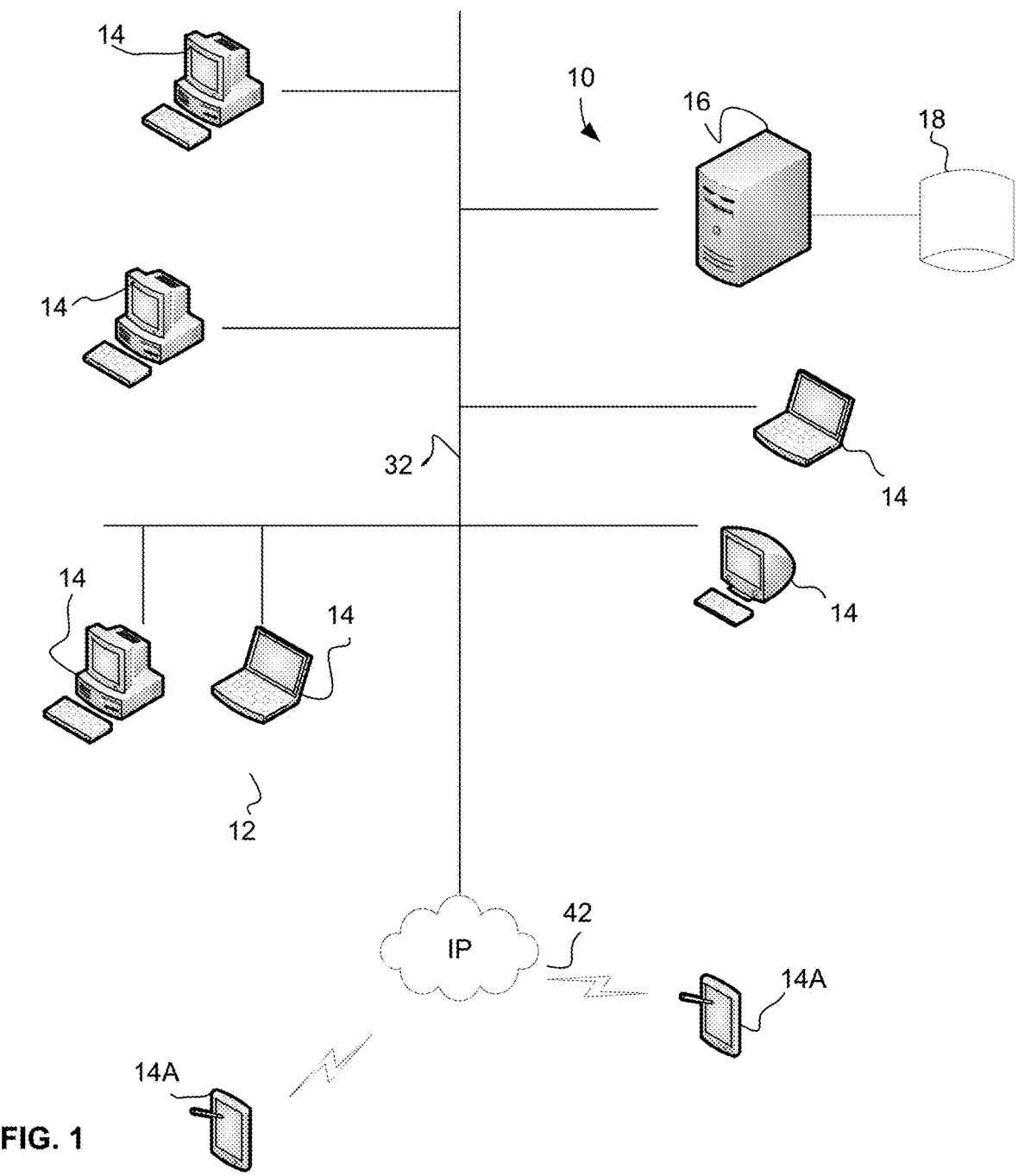
FIG. 1 is an illustration of an example block diagram illustration of a medical records system for a plurality of patients served in a medical facility.

Referring now to the drawings, one or more preferred embodiments of the present invention are next described. The following description of one or more preferred embodiments is merely exemplary in nature and is in no way intended to limit the invention, its implementations, or uses.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention.

Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Referring to FIG. 1, a representative and non-limiting example of an environment in which an implementation of the disclosed system and method can be practiced is shown in block diagram format. In particular, FIG. 1 depicts a computerized medical records system 10 that is used by clinicians (physicians, nurses and other medical personnel). The system is shown installed in a medical facility 12 indicated in dashed lines. The medical facility may for example be a hospital, nursing home, clinic, or other medical enterprise. The details on the medical enterprise and type of health care services is not particularly important.

The medical records system 10 includes a plurality of distributed workstations or client computers 14, a central server 16 and an electronic health record database 18 containing patient electronic health records (EHR). The workstations 14 could be for example general purpose computers with a processing unit and graphical display unit. The workstations 14 could also be hand-held computers. The workstations 14 include a memory storing an interactive, client-server based patient documentation application that is executed by the processor in the workstation. The application provides user interface tools in the form of graphical screen displays which allow the user access the electronic patient records stored in the database and add clinical documentation regarding a patient being treated at the facility 12.

The health care facility may have a number of patient rooms, each of which may have a workstation 14. Additionally, physicians' offices 28 may also include workstations 14, in the form of personal computers. The workstations 14 are networked on a local area network 32 wherein all of the workstations may exchange data with the central database server 16 and thereby access the patient records stored in the database 18 and write documentation and orders, prescriptions, and other information to the database 18.

The network 32 may include a router (not shown) providing a connection to an internet service provider (ISP) 40 providing access to an external wide area internet protocol network 42 such as the Internet 42. A workstation 14A may be coupled to the enterprise network 32 via the ISP 40 whereby a clinician authorized to access patient records in the database 12 may do so via the Internet 42, ISP 40 network access server and local area network 32. Thus, a workstation 14, 14A creating patient documentation need not necessarily physically reside on the network 32 or be physically located within or at the enterprise 12.

Thus, the medical records system 10 that is installed in the medical facility 12 allows clinicians to access patient records in a database 18. The preferred embodiment of such a system provides clinicians information they need, when and where they need it—at the point of care (e.g., in the patient rooms), in the offices 28, even at home via a computer 14A and the Internet 42.

Systems, methods, and computer-readable media for allowing a user/clinician to chose to either scan all medications at one time, scan them one at a time and address outstanding items, or some combination thereof, when administering medications to a patient is disclosed. In an implementation of this system and method, a User/Clinician may access via a mobile computing device an EHR system including a system application for administering medications to patients in a medical facility. The software system application displays a list of medications for administration to a patient and the user may scan in the medications in the order and manner in which the user is comfortable, thereby addressing any items relating to a scanned medication before scanning in another medication, after scanning in all medications to be administered or some combination thereof. Prior to administering the medications to the patient, the User confirms that all medications and items relating thereto have been addressed.

Figure 2:
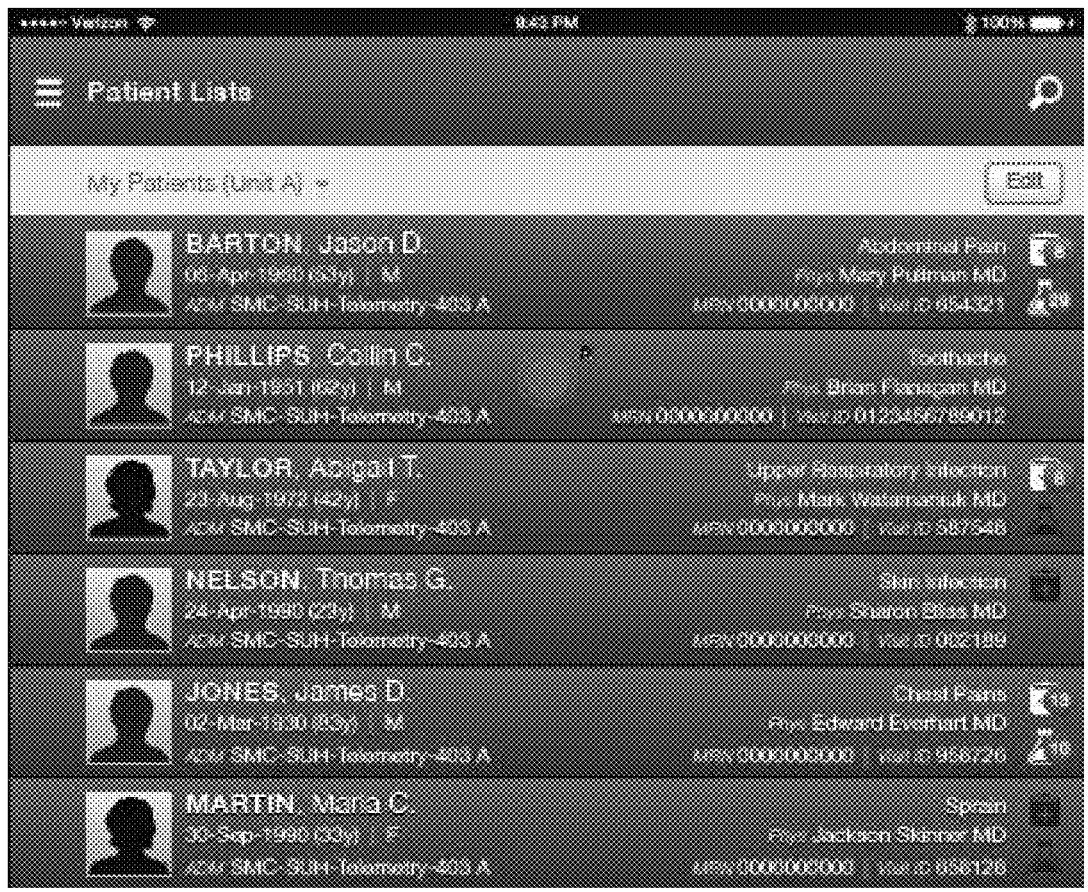
FIG. 2 is an example screenshot of an Electronic Health Care Record system application displaying a patient list in accordance with a disclosed implementation of the present invention.
Figure 3:
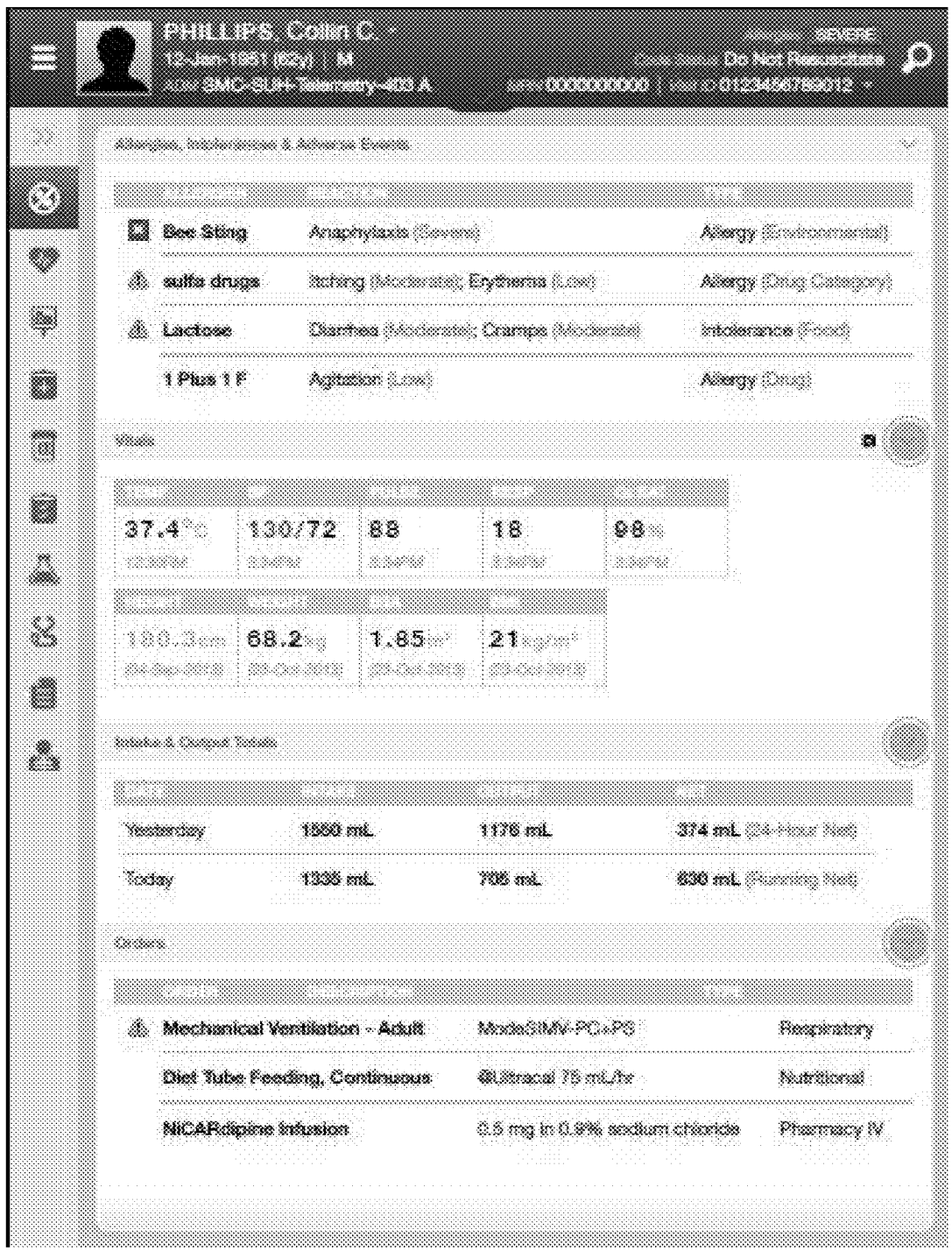
FIG. 3 is an example screenshot of a selected patient's vitals.
Figure 4:
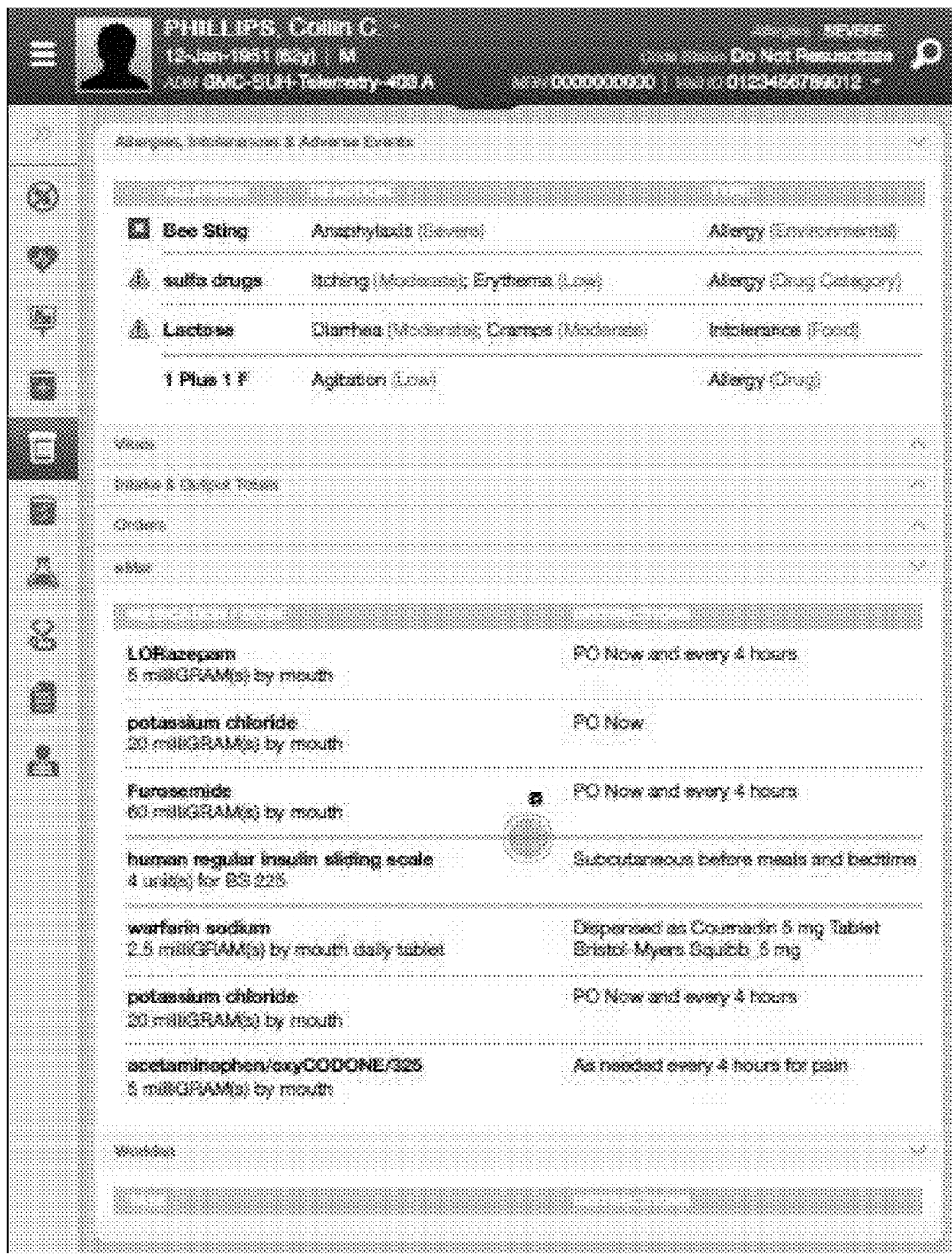
FIG. 4 is an example screenshot of FIG. 3 including a medications/Dose section in accordance with a disclosed implementation of the present invention.

An example implementation of the disclosed system and method is illustrated in FIGS. 2-22. When a User (e.g., a Nurse) is about to encounter a patient to administer medications, the UI for a system application, such as in an Electronic Health Record (EHR) system, displays a list of patients for selection by the nurse. An example of a screen shot of the EHR system application displaying a patient list is illustrated in FIG. 2. The nurse may then select the patient's name, e.g., PHILLIPS, Collin C., that the nurse is visiting to administer medications. Once the patient is selected a view of the patient's vitals and other patient information may be displayed. An example screen shot of the selected patient's vitals is shown in FIG. 3. The nurse may collapse the vitals I/O Totals and Orders sections in order to view the medications section for the patient in context. See FIGS. 4 and 5. FIG. 4 is an example screen shot of FIG. 3 including the medications/Dose section. The nurse may then click or tap anywhere within the medication/Dose section to view a full screen of the medication/Dose section, as illustrated in FIG. 5.

Figure 5:
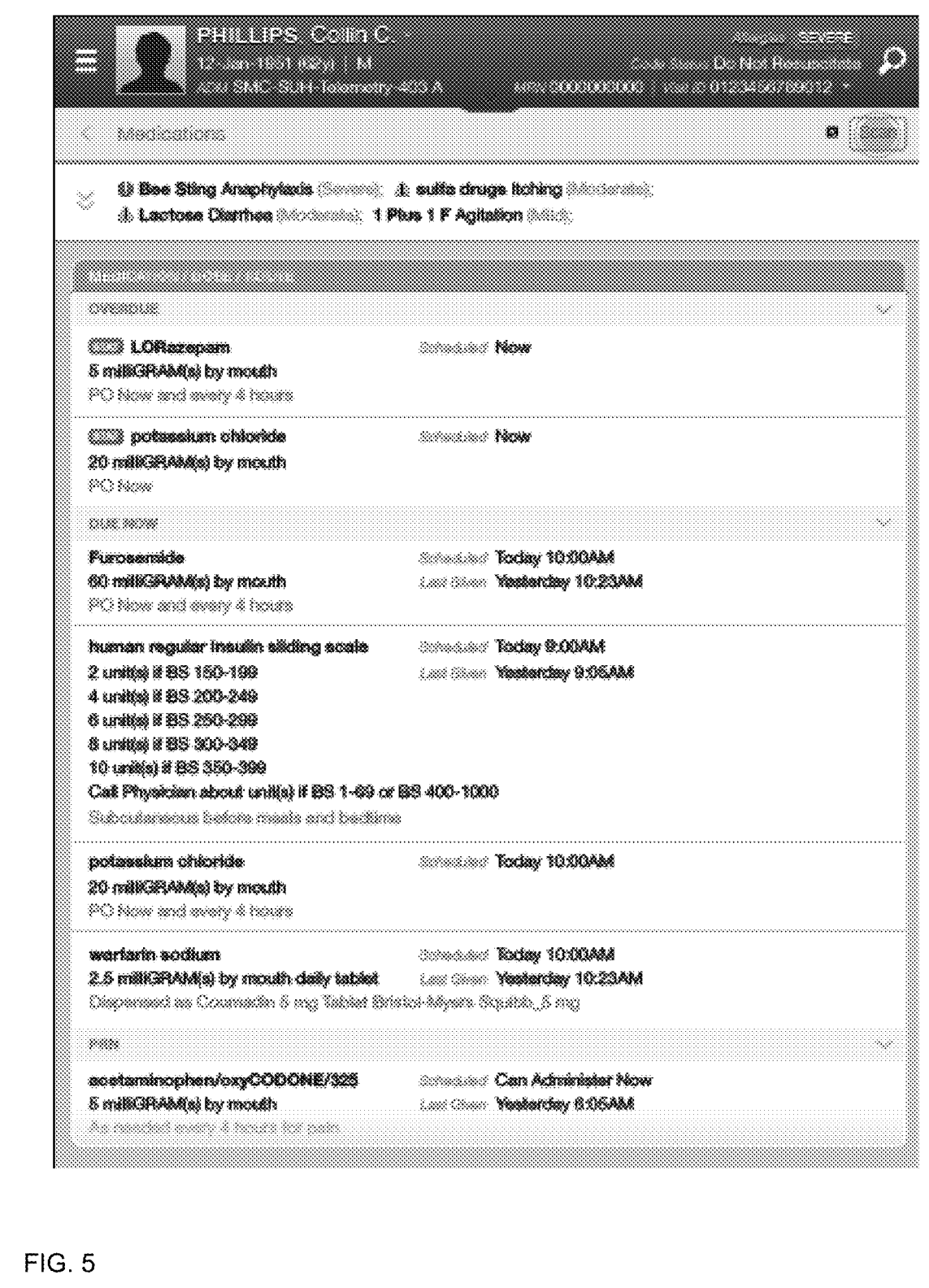

As illustrated in FIG. 5, the nurse may use this screen to review what medications are overdue, Due Now, PRN and Upcoming. This example screenshot may also be used by the nurse to pull the medications the nurse will need to administer to the patient.

When the nurse is ready to administer the medications to the patient, the nurse may tap/click the scan button 602.

Figure 6:
FIG. 6 is an example screenshot of a scan window.

In this example, a Scan Window 710 opens that allows the nurse to scan the patient's wrist band, for example, to confirm who the patient is. An example screen shot of the scan window is illustrated in FIG. 6.

If the scanned patient is not a match, the nurse may be directed to try the scan again or select the patient that has been scanned.

Figure 7:
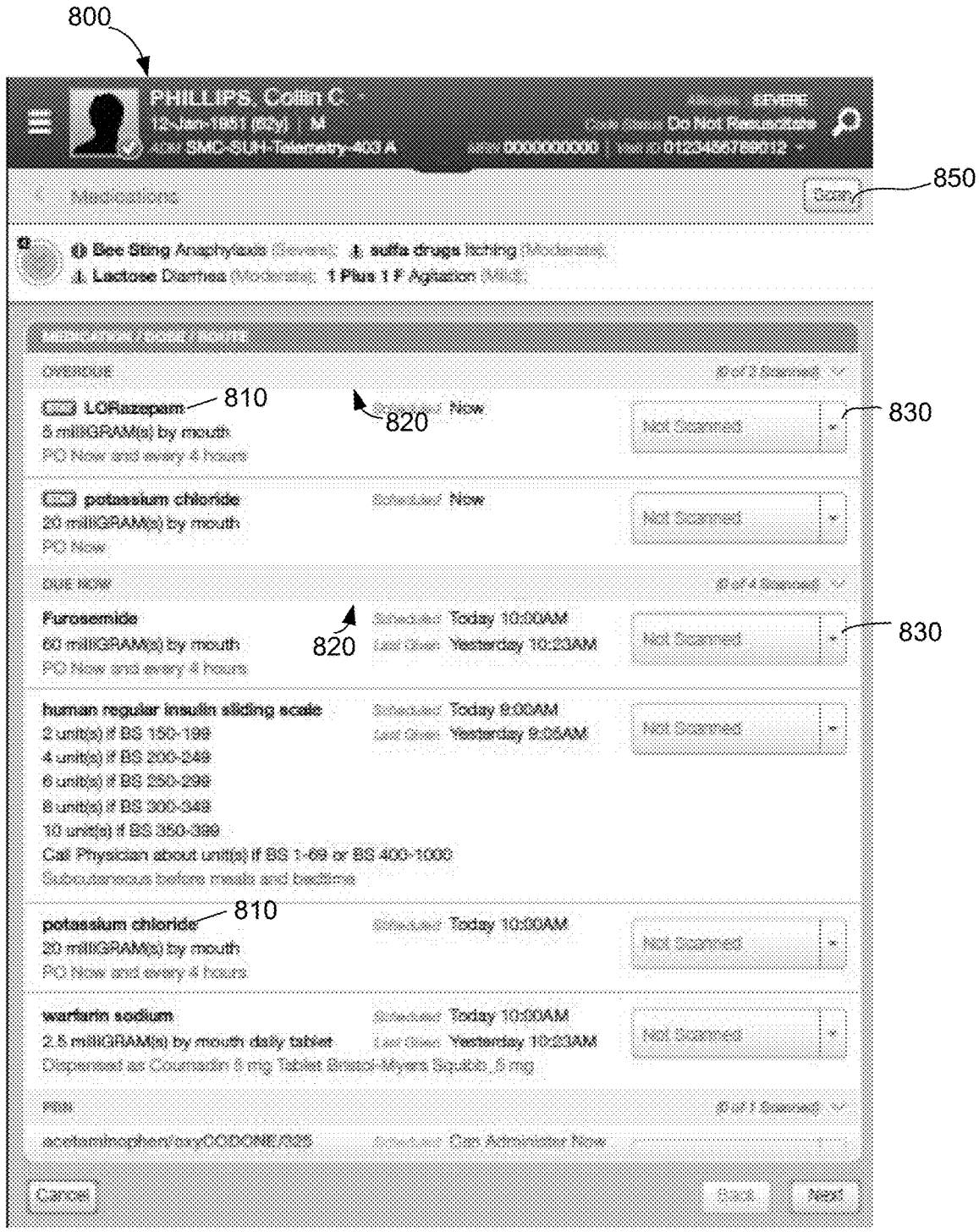
FIG. 7 is an example screenshot of the MED ADMIN User Interface in accordance with a disclosed implementation of the present invention.

If the patient is a match to the selected patient, the nurse may start scanning in medications. A Med Admin UI, similar to the Medication/Dose section illustrated in FIG. 5, is displayed to the nurse that allows the nurse to scan in medications and address medication specific items. An example screen shot of the Med Admin UI 800 is illustrated in FIG. 7. The Med Admin UI 800 includes one or more medications 810, one or more medication sections, e.g., Medications Overdue, Due Now, etc., and a Status Box 830 associated with each medication 810.

Figure 8:
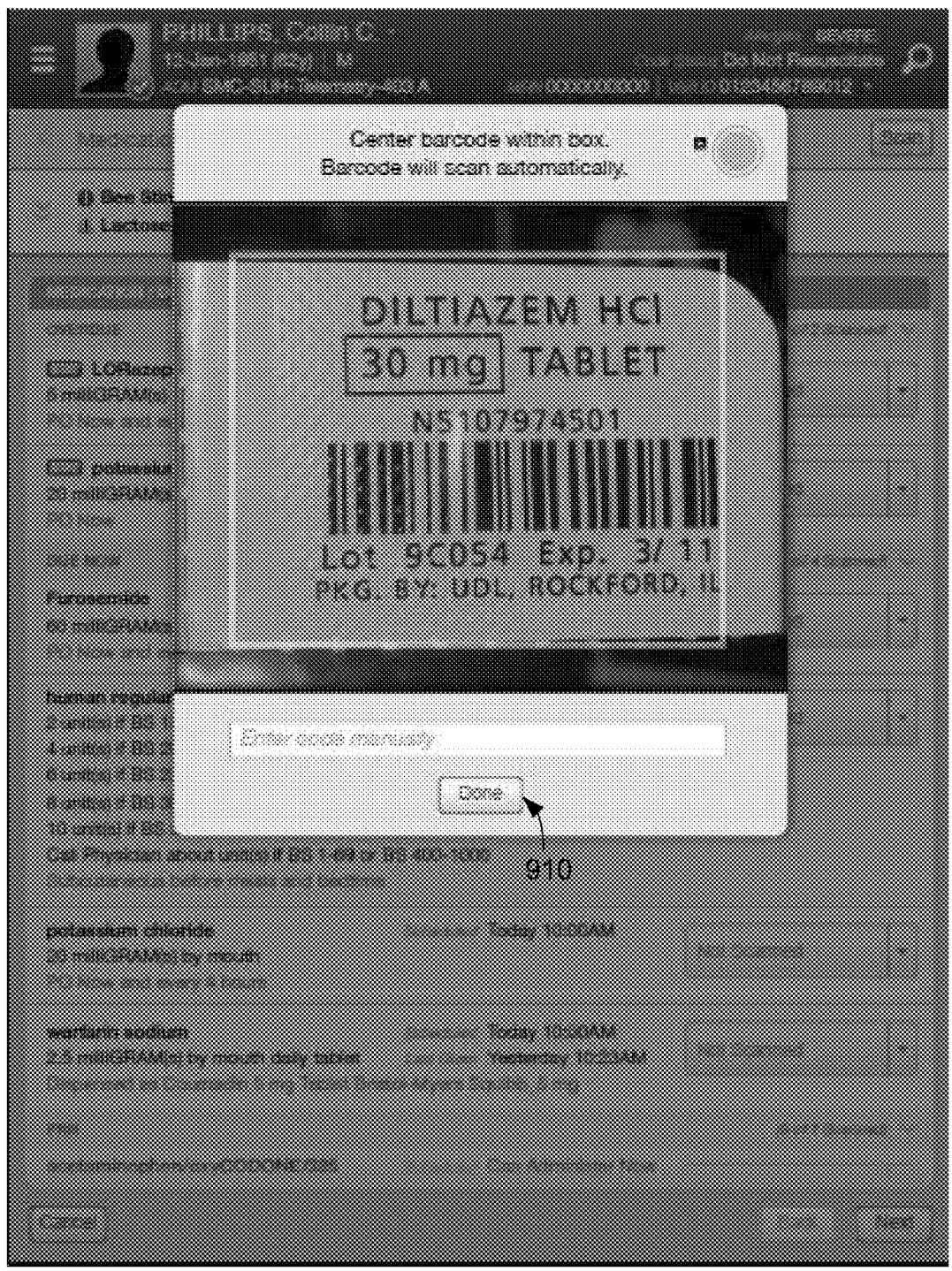
FIG. 8 is an example screenshot of a scan pop-up window.

To begin scanning in medications, the nurse may tap/click the scan button 850. When the scan button 850 is selected, the nurse is asked to scan a medication, preferably through a pop-up window that allows the nurse to align the barcode of the medication within the window in order to scan the barcode. An example screen shot of the scan pop-up window 900 is illustrated in FIG. 8.

Figure 9:
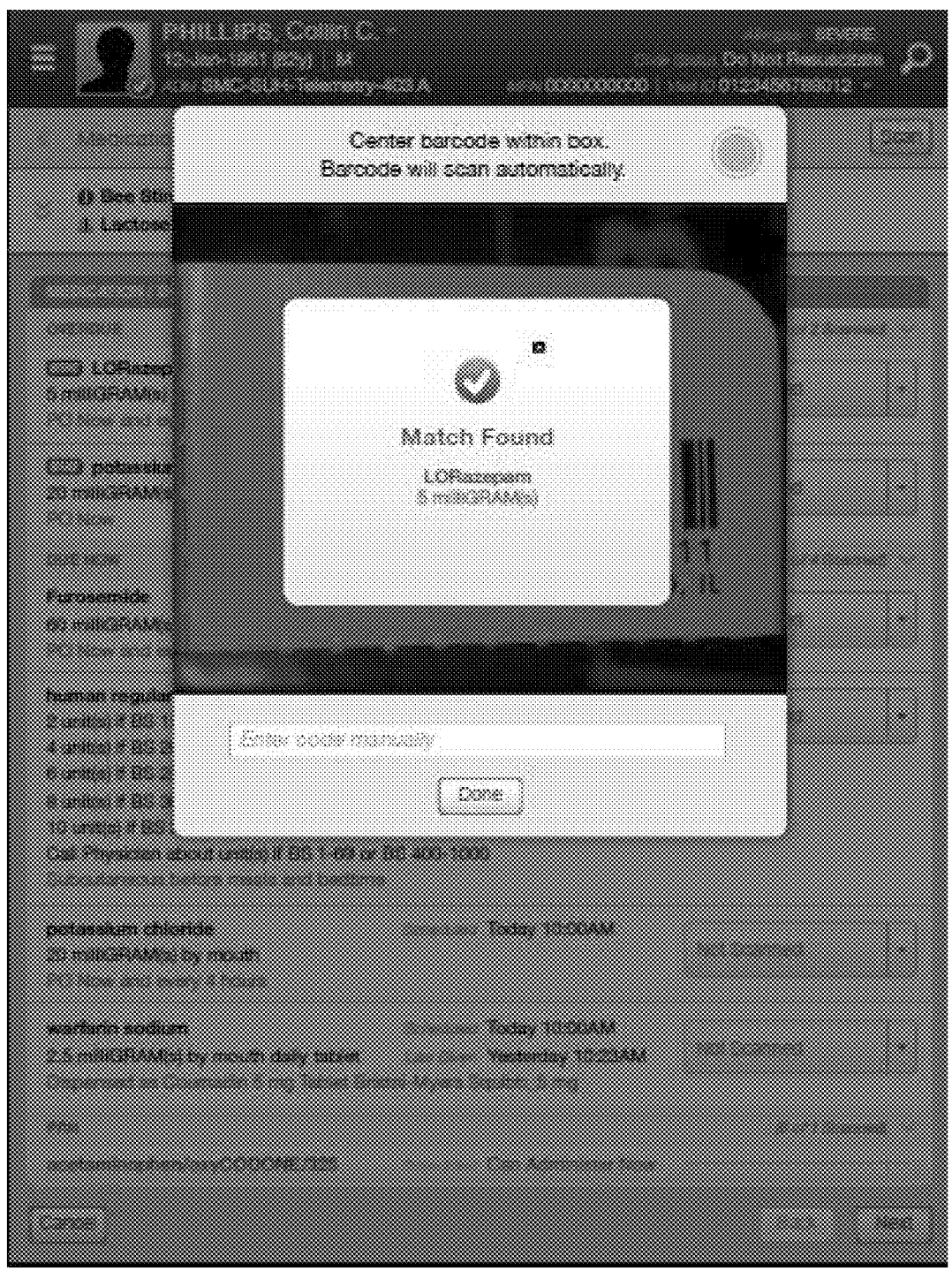
FIG. 9 is an example screenshot of a match indication displayed to a nurse.
Figure 10:
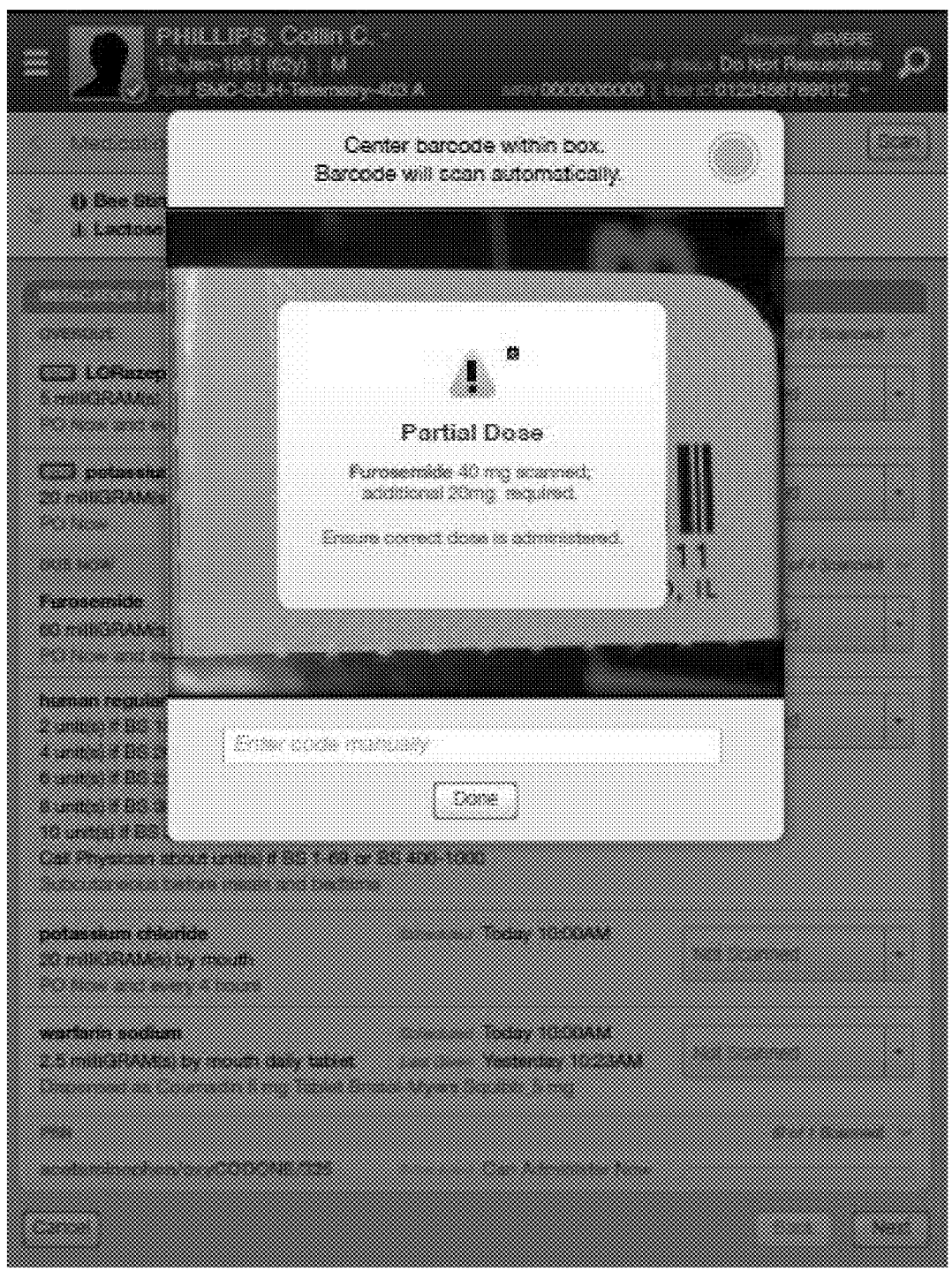
FIGS. 10-13 are example screenshots of indication pop-up windows.
Figure 11:
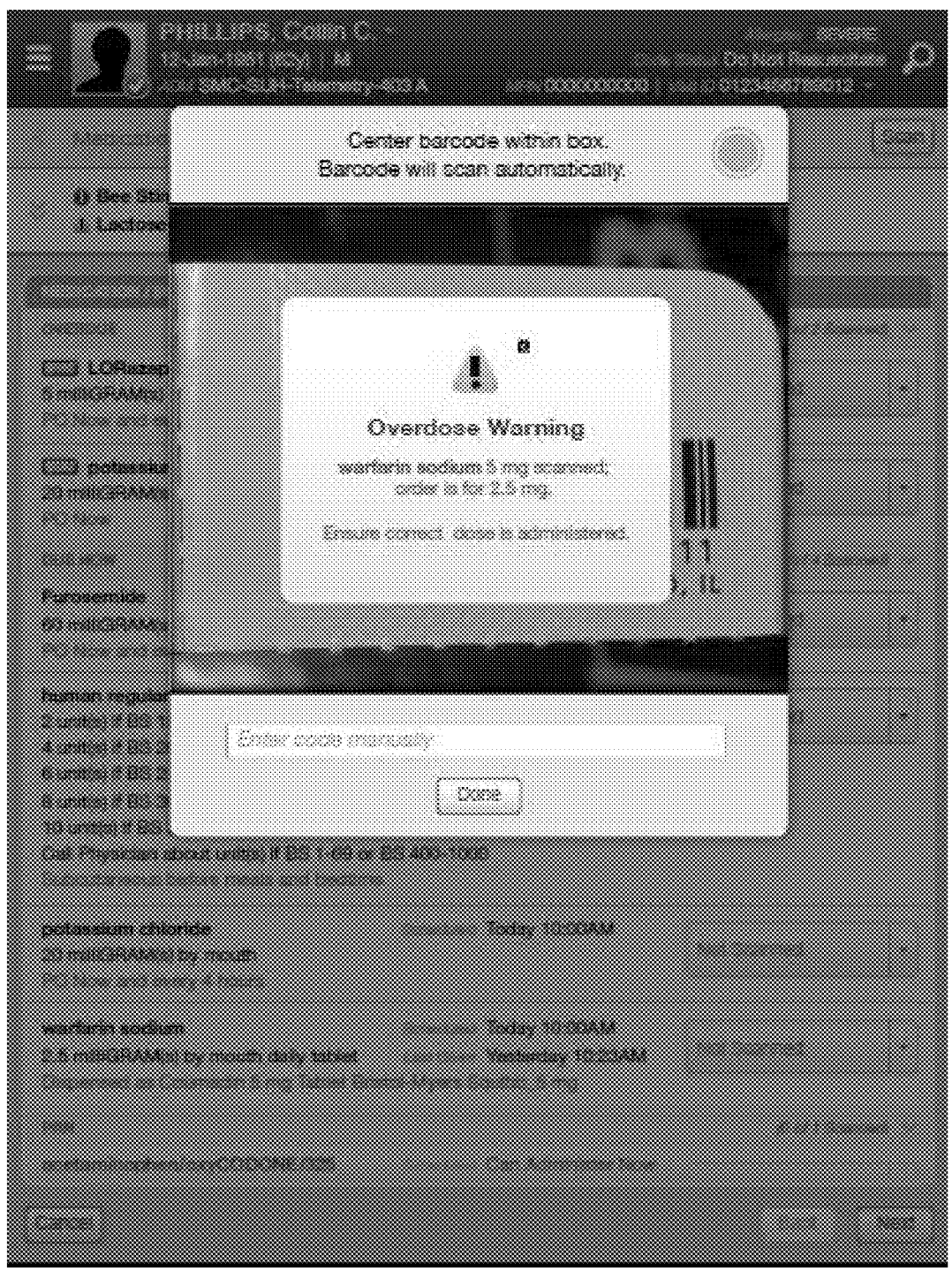
Figure 12:
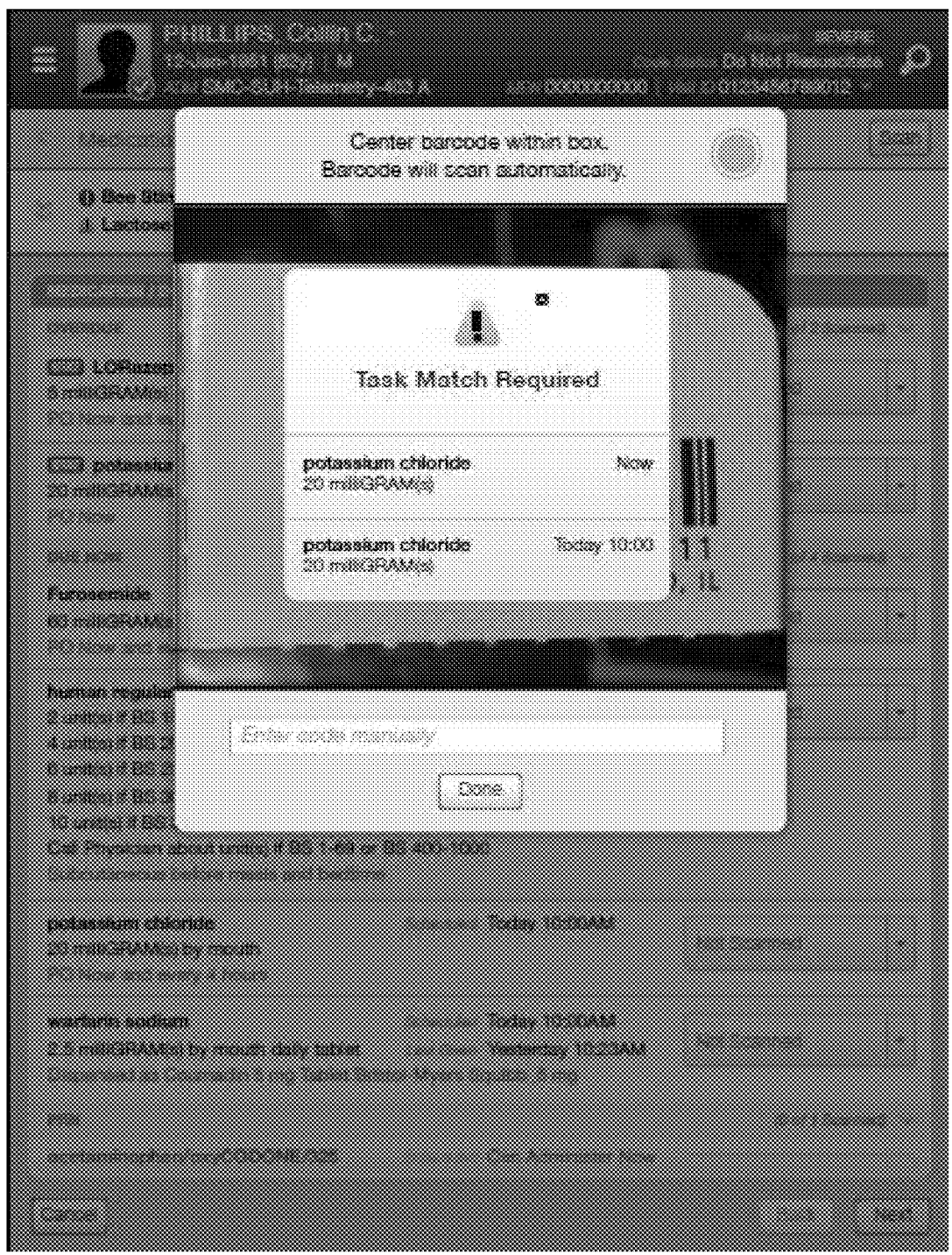
Figure 13:

Once the nurse has aligned the barcode within the scan pop-up window 900, the nurse may tap/click the Done button 910. A confirmation that the scanned medication is to be administered to the patient is conducted. If a match is found, a match indication is displayed to the nurse. An example screen shot of the match indication displayed to the nurse is illustrated in FIG. 9. In the example, the nurse has scanned LORazepam and a match was found.

It is preferable that the pop-up match indication that is displayed on the screen dismisses automatically and provides a confirmation to the nurse. The Med Admin UI screen also updates with the match information. In accordance with the disclosed implementation, any scans that require attention are addressed from the main screen, not the scan window.

The nurse may close the scan window and address individual medications whenever the nurse chooses. The disclosed system and method allows the nurse to either scan all medications and address any issues all at once, address the issues for each medication as they appear, or some combination thereof.

If there is an issue that must be addressed with a scanned medication, the indication pop-up window displayed to the nurse will include a description of the issue. As indicated, the indication pop-up window will preferably disappear. The nurse then will have the option of addressing the issue by going back to the Med Admin UI or scanning in the next medication and addressing the issue at a later time. Example screenshots indication pop-up windows displaying an issue to the nurse are illustrated in FIGS. 10-13. Again, it is preferable that each of the indication pop-up windows illustrated in FIGS. 10-13 automatically disappears after a predetermined amount of time.

When the nurse has completed scanning in all medications or wants to address an issue that was displayed for a medication, the nurse closes out of the scan pop-up window, illustrated in FIG. 8. The Med Admin UI is then displayed again to the nurse.

As indicated above, once the nurse has scanned in any medications, the indication that is displayed to the user in the indication window is also updated in the Med Admin UI via the Status Box. An example screen shot of the Med Admin UI including updated Status Boxes after one or more medications have been scanned in by the nurse is illustrated in FIG. 14.

Figure 14:
FIG. 14 is an example screenshot of the Med Admin including updated Status Boxes in accordance with a disclosed implementation of the present invention.

As illustrated in FIG. 14, the Status Box 1530 displays a status message 1531 and a status symbol 1535. In a preferred implementation, the Status Box 1530 would also indicate the status by the color of the Status Box 1530. For example, a Critical Warning status message would result in the Status Box 1530 being RED; a Match Complete status message would result in a green Status Box 1530; and a Match Required message would result in a yellow Status Box 1530.

Figure 15:
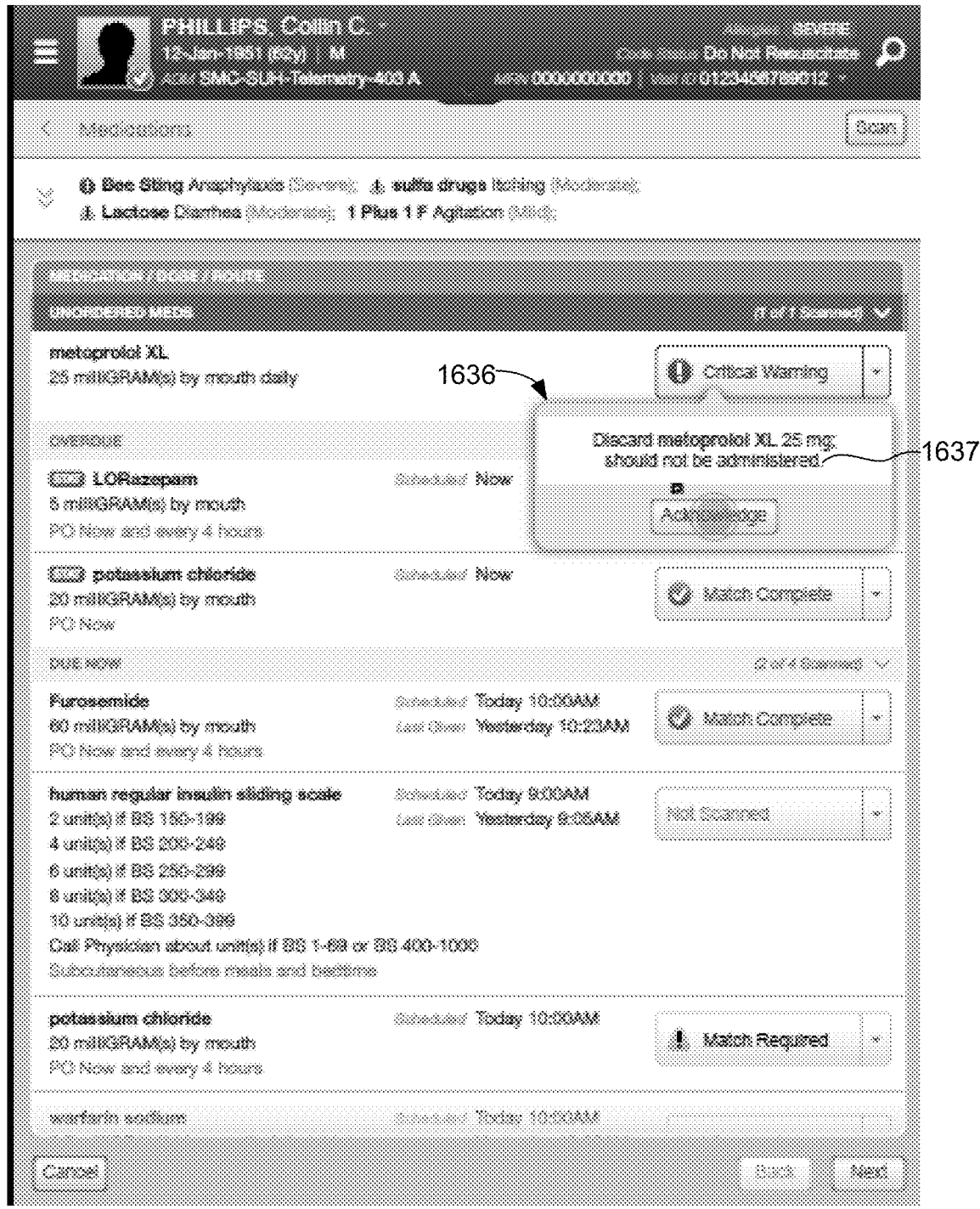
FIG. 15 is an example screenshot of the Med Admin UI including a message window in accordance with a disclosed implementation of the present invention.

In order for the nurse to view the status message 1531 and address the issue, the nurse may select the status message 1531 by tapping/clicking on the appropriate Status Box 1530. When the nurse selects the Status Box 1530, a message window may pop up including an issue message that provides the nurse with information relating to the outstanding item that needs to be addressed. An example screen shot of the Med Admin UI including the message window is illustrated in FIG. 15.

As illustrated, the message window 1636 includes the issue message 1637. The issue message 1637 may include an action to be taken by the nurse or require the nurse to acknowledge that the nurse has performed an action. In this example, the nurse must acknowledge that he/she has read and understands the issue message 1637.

Figure 16:
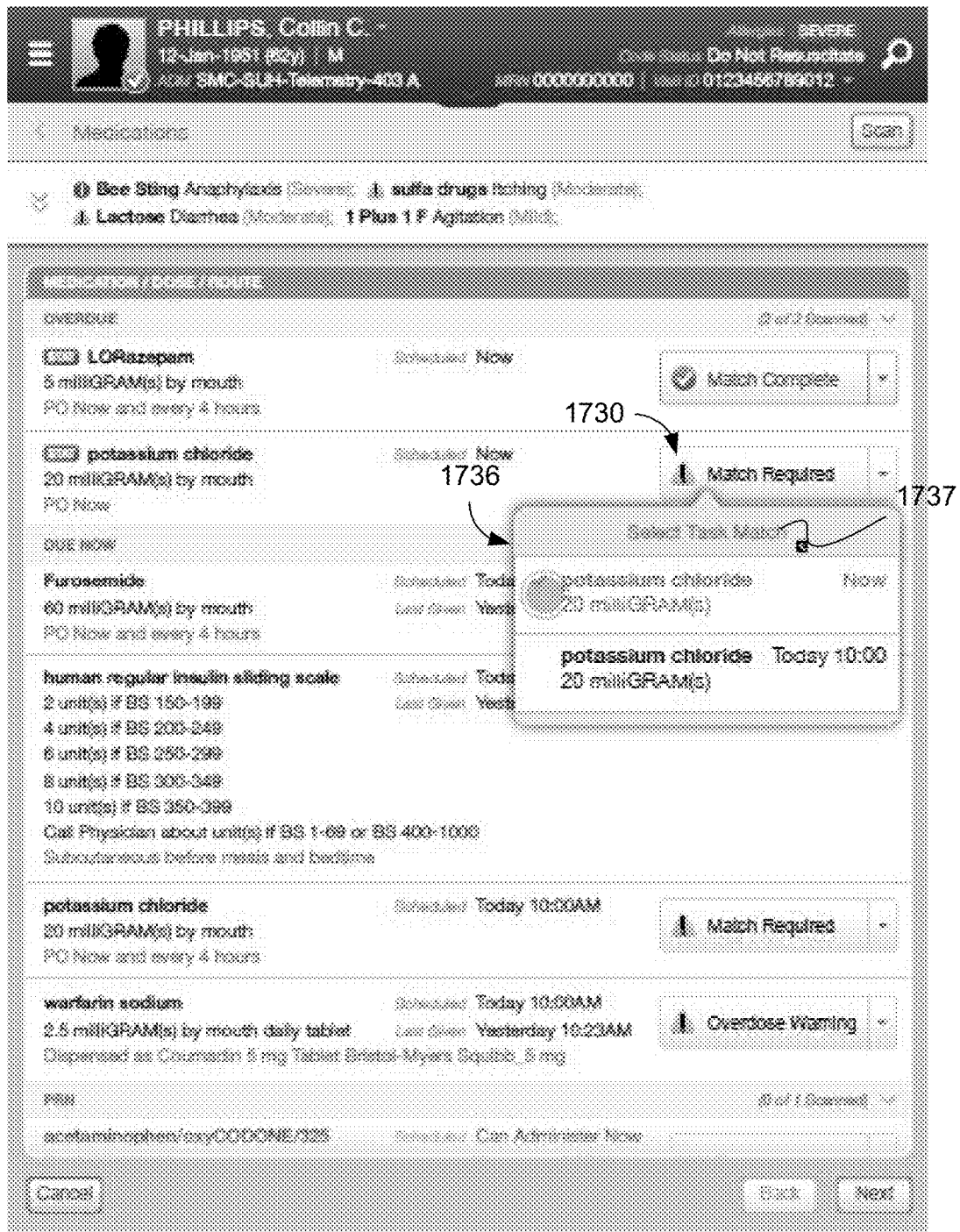
FIG. 16 is an example screenshot of an issue message.

FIG. 16 is an example screen shot of an issue message 1737 that requires the nurse to select a medication from a list of medications displayed in the message window 1736. In this example, the nurse selects the appropriate medication by tapping/clicking on the medication.

Figure 17:
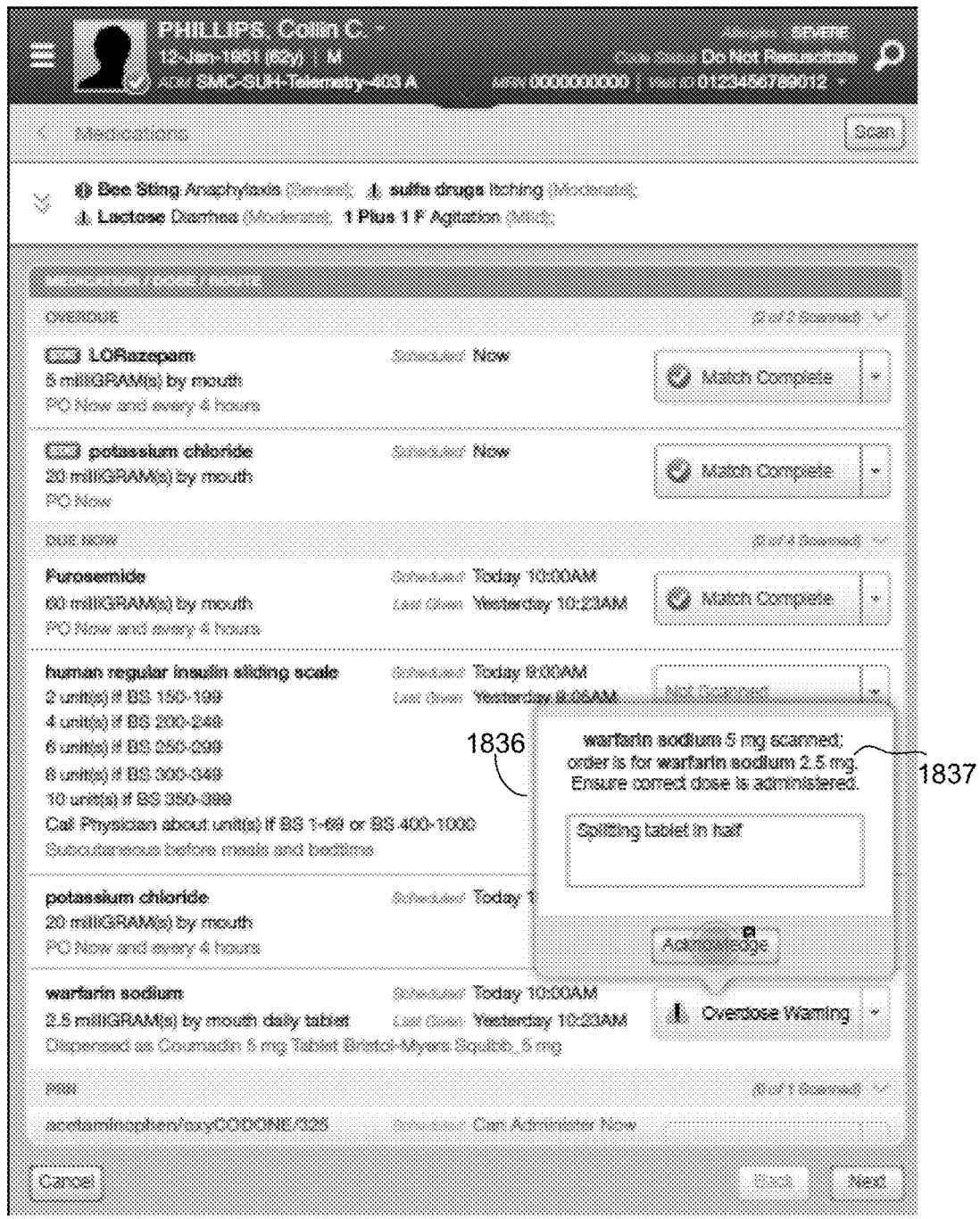
FIG. 17 is an example screenshot of an issue message that includes issue information.

FIG. 17 is an example screen shot of an issue message 1836 that includes the issue information and requires the nurse to input some information and Acknowledge the message.

Once the nurse addresses the issue within the message window, the status indicator within the Status Box is changed to reflect the new status of the scanned medication.

Figure 18:
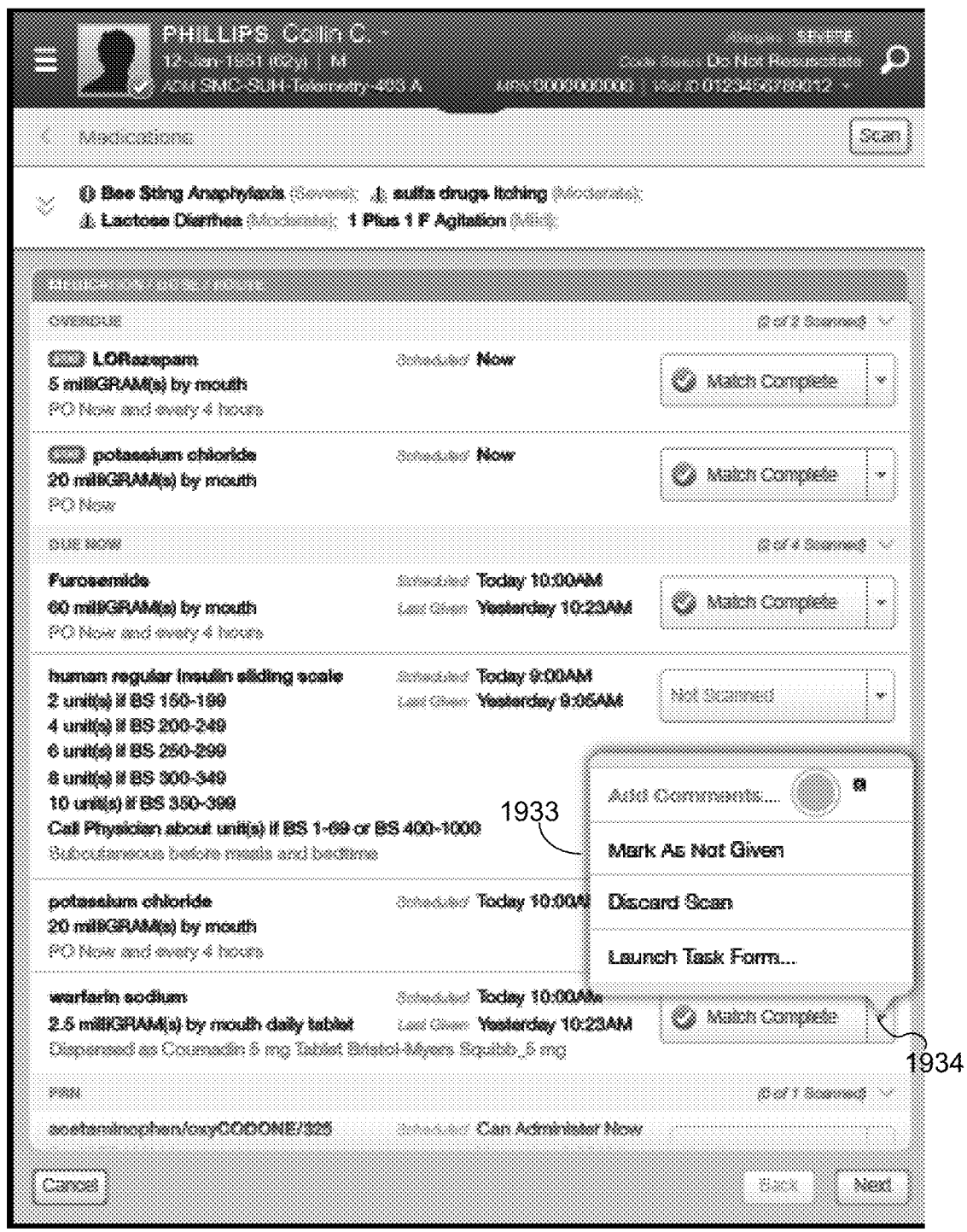
FIG. 18 is an example screenshot of the Med Admin UI including a selected Action Arrow in accordance with a disclosed implementation of the present invention.

Referring back to FIG. 7, each Status Box 830 includes an Action Arrow 834. The Action Arrow 834, when selected by the nurse, displays to the nurse actions that may be completed for the respective medication. Accordingly, when the nurse selects the Action Arrow 830 an Action Window is displayed that lists the actions the nurse may complete. An example screen shot of the Med Admin screen including a selected Action Arrow 1934 and the resulting Action Window 1933 is illustrated in FIG. 18. The Action Arrow 1933 illustrated in this example includes the actions Add Comments, Mark As Not Given, Discard Scan, and Launch Task Form.

Figure 19:
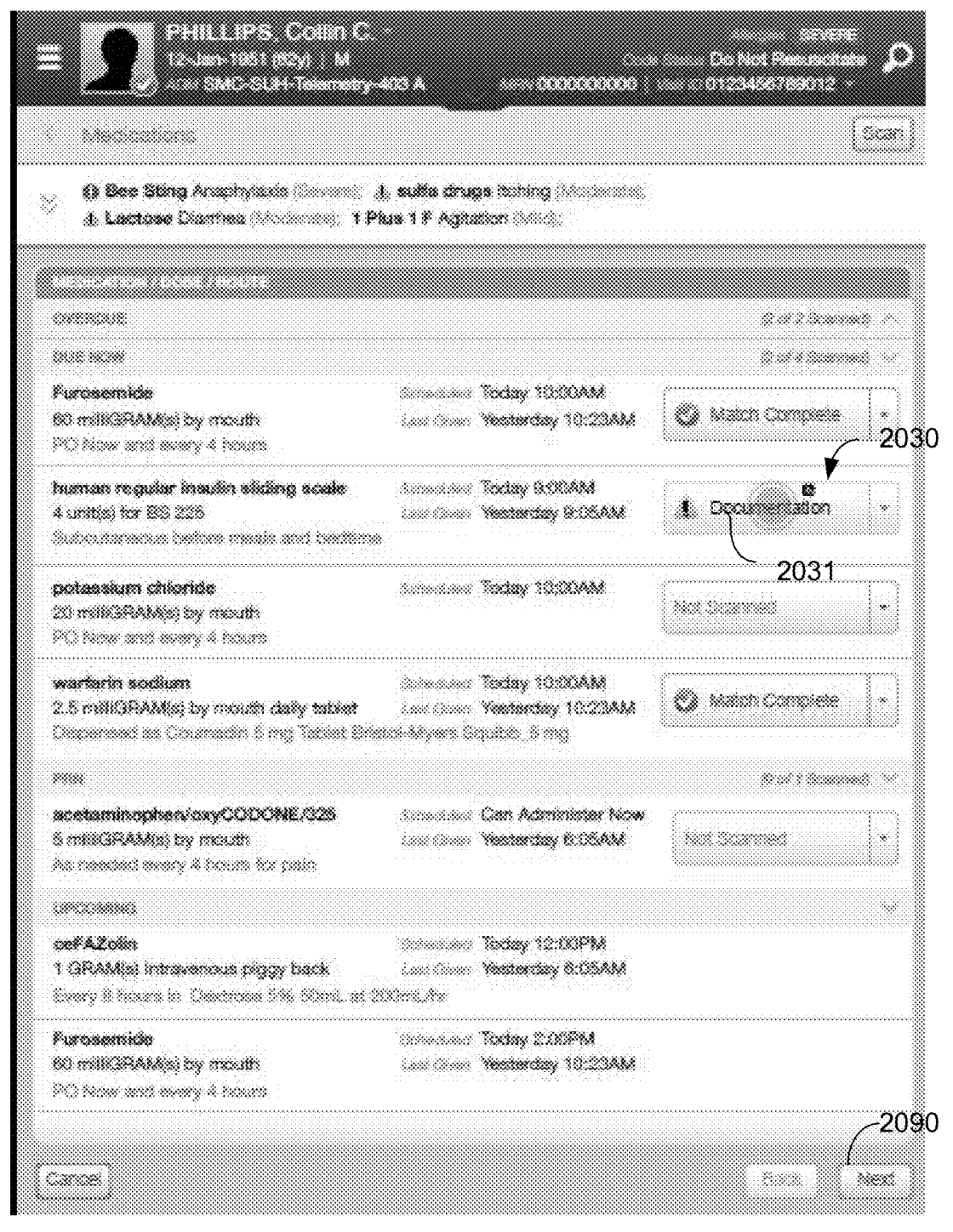
Figure 20:
FIG. 20 is an example screenshot of an issue message resulting from selecting the Status message shown in FIG. 19.

FIG. 19 is an example screen shot of the Med Admin screen wherein a Status Box 2030 includes the Status message 2031, DOCUMENTATION. When the nurse selects the Status message 2031, an issue message is displayed to the nurse. An example screen shot of the resulting issue message 2136 is illustrated in FIG. 20. As illustrated, the nurse is required to input information and Save. A virtual keyboard 2180 may also be displayed for the nurse to input the required information.

Figure 21:
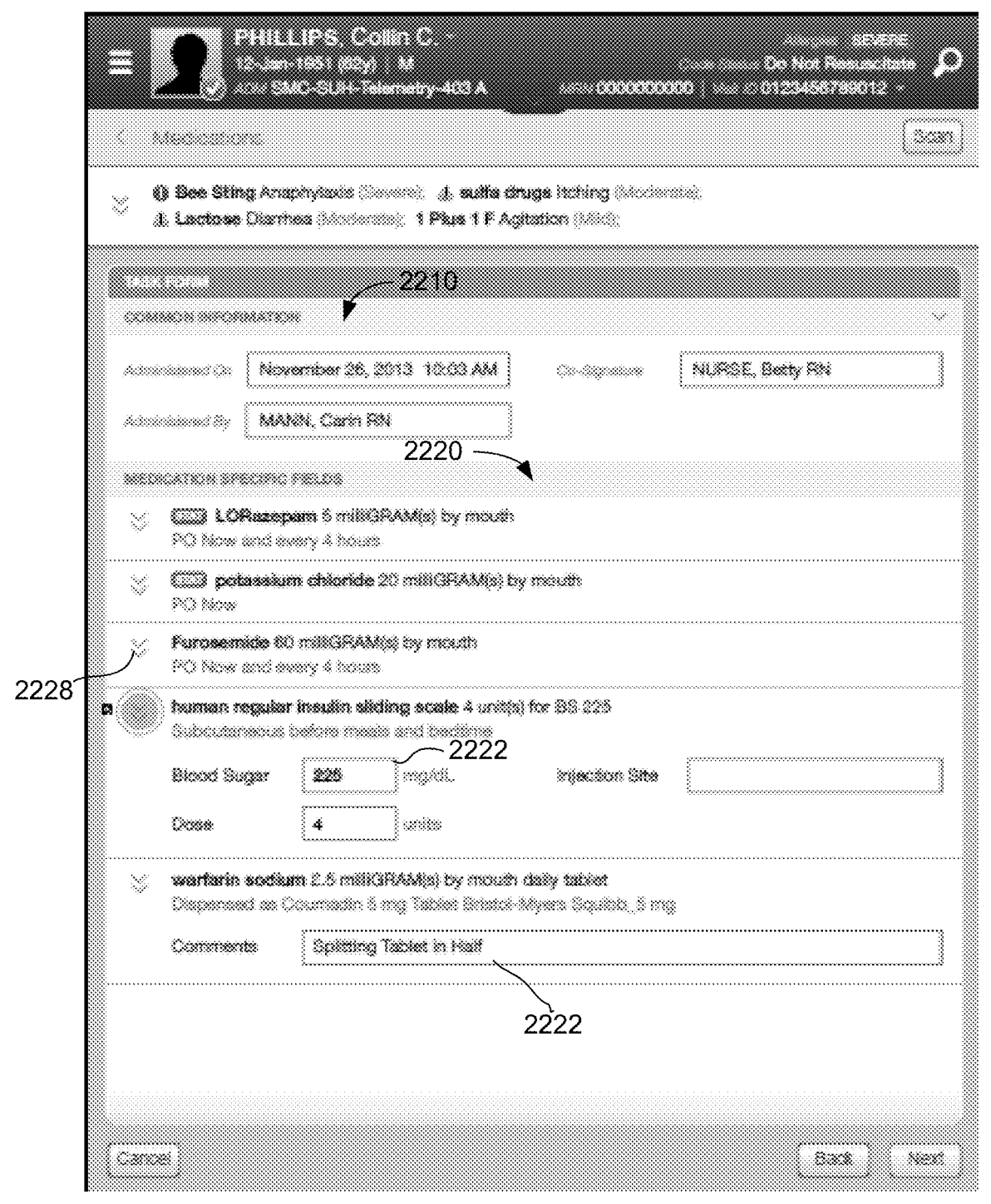
Figure 22:
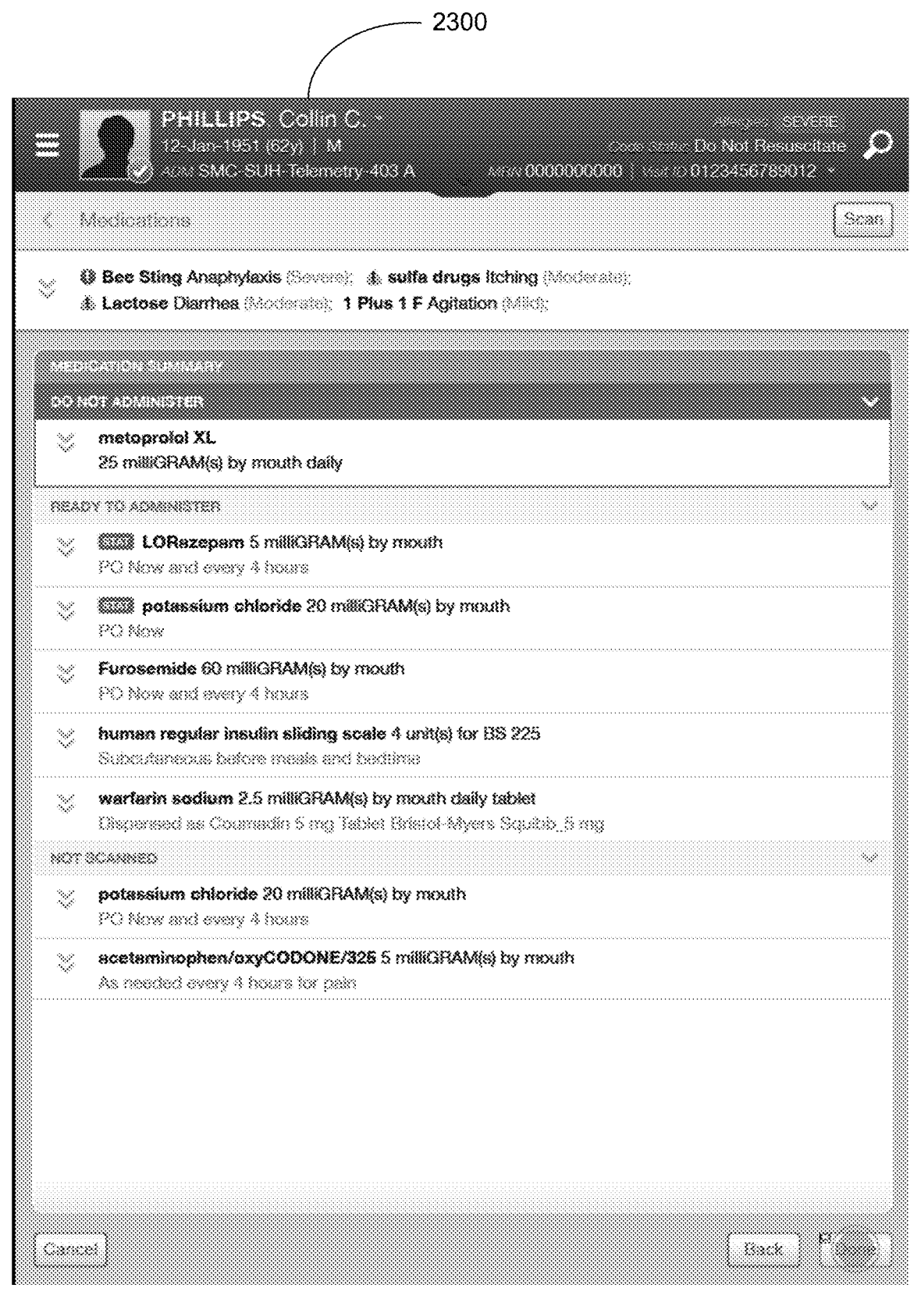

Referring back to FIG. 19, once all of the warnings have been addressed in the Med Admin screen by the nurse, the nurse may go to the next step in the Med Admin workflow, Task Forms, by selecting the NEXT Button 2090. An example screen shot of the Task Form screen is illustrated in FIG. 21. As illustrated in FIG. 22, the Task Form screen 2200 includes a Common Information section 2210 and medication specific fields section 2220. Fields that are common in the medication (Med) Task Form are included in the Common Information section 2210. Required fields for the specific medication(s) are included in the medication specific field section 2220. It is preferable that the specific fields 2222 are displayed below the medication for which the field 2222 is required. The Med specific field section 2220 further includes a chevron 2228, located next to the medication name that allows the nurse to view individual task forms when the nurse taps/clicks on the chevron 2228. A detailed description of the Task Form is disclosed in pending U.S. patent application Ser. No. 14/556,193, filed Nov. 30, 2014, entitled "SYSTEM AND METHOD FOR ADMINISTERING MEDICATIONS", which is incorporated by reference as if fully set forth herein.

When the nurse has reviewed all of the items in the Task Form for each medication, the nurse may tap/click the NEXT button to go to review the Medication Summary. An example screen shot of the Medication Summary is illustrated in FIG. 22. The Medication Summary allows the user to review the summary of the scans. The Summary 2300 shows the nurse the meds that should NOT be administered, are ready to be administered, and those that were not scanned. The nurse then selecting DONE marks all of the items complete.

Figure 23:
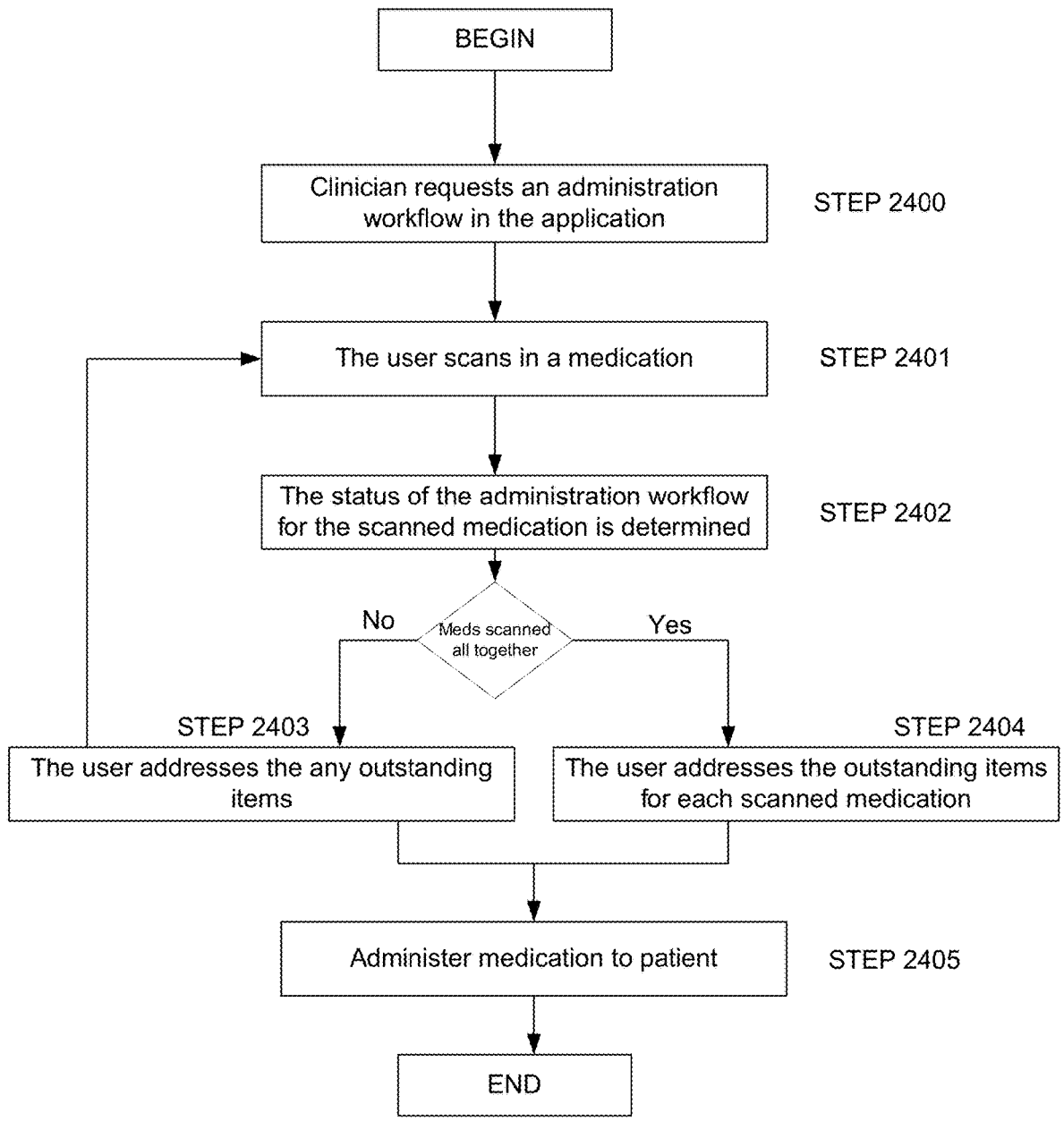
FIG. 23 is an example flow diagram of an implementation of the disclosed system and method in accordance with the present invention.

An example flow diagram of the disclosed implementation is shown in FIG. 23. A clinician begins a medication administration workflow in a system application. (STEP 2400). The user scans in a medication which is then added to a list of medications that are displaying in the UI. (STEP 2401). The status of the scanned in medication is then determined by the application. (STEP 2402). If the user chooses to scan in the medications one at a time, the user then addresses any outstanding items that are displayed to the user via a status indicator associated with the scanned in medication, (STEP 2403), and then scans the next medication. (STEP 2401).

If the user chooses to scan in all medications prior to addressing any outstanding items for each medication, the user addresses the outstanding items for each scanned in medication after all medications have been scanned in. (STEP 2404).

Once the outstanding items have been addressed for a medication, the user is able to administer the specific medication. (STEP 2405).

Figure 24:
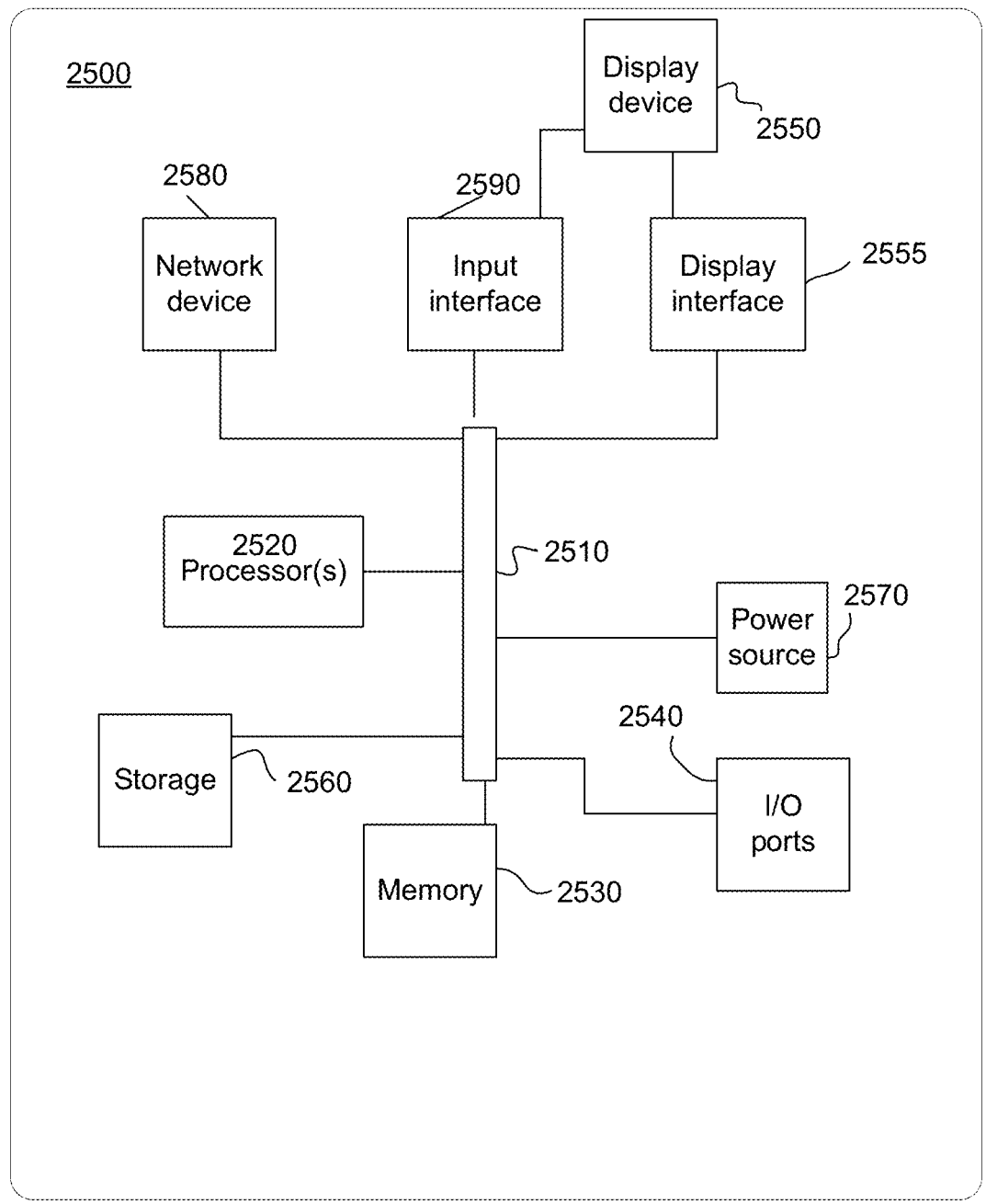
FIG. 24 is an example illustration of a suitable computing device operable in accordance with an implementation of the disclosed system and method.

An example of a suitable computing device operable in accordance with an implementation of the disclosed system and method is illustrated in FIG. 24. It should be noted that the various functional blocks shown in FIG. 24 may include hardware elements, software elements (including computer code or instructions stored on a non-transitory machine-readable medium) or a combination of both hardware and software elements. The computing device 2500, may be implemented in different forms. For example, the computing device 2500 may be implemented as a server, group of servers, a desktop computer, laptop, workstation, personal digital assistant (PDA) and other appropriate computers. The computing device 2500 includes a bus 2510, display interface 2555, display device 2550, I/O ports 2540, Input interface 2590, data processing circuitry, such as one or more processors 2520, a memory device 2530, a non-volatile storage 2560, a networking device 2580 and a power source 2570.

The computing device may also be implemented as a mobile computing device. The mobile computing device may be implemented by various mobile devices, such as PDAs, cellular phones, smart phones, tablets and other similar computing devices. The mobile computing device includes a bus, a display, I/O ports, Input displays, one or more processors, a memory device, a non-volatile storage, a networking device, a power source, and a transceiver for implementing wireless communication under various protocols, such as SMS or MMS messaging, CDMA, TDMA, WCDMA or GPRS, among others. The components of the computing devices as shown, their connections and relationships and their functions are meant for exemplary purposes only, and are not meant to limit implementations of the disclosed inventions described and/or claimed in this disclosure.

The display device 2550 may be used to display images generated by the computing device 2500, for example a graphical user interface (GUI). The display 2550 may be any type of display such as a cathode ray tube (CRT), a liquid crystal display (LCD), a light emitting diode (LED) display, or other suitable display. In certain implementations of the computing device 2500, the display 2550 may include a touch-sensitive element, such as a touch screen.

The processor(s) 2520 may provide data processing capability to execute and support one or more operating systems, computer programs, user and application interfaces, software systems and applications, and any other functions of the computing device 2500 that may be stored in the memory device 2530 or on the storage device 2560. The processor(s) 2520 may include one or more microprocessors, such as one or more "general-purpose" microprocessors, one or more special-purpose microprocessors and/or ASICS, for example.

The processor(s) 2520 may communicate with a user through input interface 2590 and display interface 2555 coupled to the display 2550. The display interface 2555 may comprise appropriate circuitry for driving the display 2550 to present graphical and other information to a user. The input interface 2590 may receive commands from a user and convert them for submission to the processor 2520.

The instructions or data to be processed by the processor(s) 2520 may be stored in a memory 2530. The memory 2530 may be provided as a volatile memory, such as random access memory (RAM), and/or as a non-volatile memory, such as read-only memory (ROM). The memory 2530 may store a variety of information and may be used for various purposes. For example, the memory 2530 may store firmware executed by a processor 2520 (such as a system and method for implementing a medication administration workflow as discussed herein), other programs that enable various functions of the computing device 2500, user interface functions, processor functions. The memory 2530 may also be another form of computer-readable medium.

The components may further include a non-volatile storage 2522 for persistent storage of data and/or instructions. The non-volatile storage 2522 may include flash memory, a hard drive, or any other optical, magnetic, and/or solid-state storage media. The non-volatile storage 2522 may be used to store data files, software, wireless connection information (e.g., information that may enable the computing device 2500 to establish a wireless connection, and any other suitable data. In addition, the non-volatile storage 2560 may also store code and/or data for implementing various functions of the computing device 2510, such as application or program code, data associated with such applications or programs, operating system code, user configured preferences, as well as code for implementing a medication administration workflow as discussed herein. In implementation, the storage device 2560 may be or contain a computer-readable medium. A computer program product can be tangibly embodied in an information carrier. The computer program products may also contain instructions that, when executed, perform one or more methods, such as those described above. The information carrier is a computer- or machine-readable medium, such as the memory 2530, the storage device 2560, memory on processor 2520, or a propagated signal.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

The disclosed system and methods are preferably implemented by software, hardware, or a combination of hardware and software. The disclosed implementations can include implementation in one or more computer programs that are executable and/or interpretable on a programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in an appropriate programming language. As used herein, the terms "machine-readable medium" "computer-readable medium" refers to any computer program product, apparatus and/or device (e.g., magnetic discs, optical disks, memory) used to provide machine instruction and/or data to a programmable processor. The computer readable medium can also be distributed over network-coupled computer systems so that the computer readable code is stored and executed in a distributed fashion.

The implementation of the disclosed system and method provides the user with the ability to scan multiple medications at one time, thereby assisting in accommodating the interruptions that are a part of a nurses/clinicians practice and making medication administration safer and more efficient.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof

What is claimed is:

1. A mobile electronic device comprising a display and a computer readable medium storing a computer program for providing a medication administration workflow in a user-interface (UI), the computer program executable by at least one processor, the computer program comprising sets of instructions for facilitating a method comprising:
   displaying, to a healthcare provider user via the display, an interface of an electronic health record (EHR) software application comprising a listing of patients;
   receiving, from the healthcare provider user via the interface, first user input corresponding to a selection of a first patient included in the listing of patients;
   receiving, from the healthcare provider user via the interface, second user input corresponding to engagement with a scan button;
   displaying, to the healthcare provider user via the display in response to the received second user input corresponding to engagement with the scan button, a scan window that includes an image captured by the mobile electronic device and allows the healthcare provider user to scan a wrist band of a patient by positioning the mobile electronic device to align the barcode of the wrist band within the scan window;
   capturing, via the mobile electronic device, the barcode of the wrist band;
   determining, based on the captured barcode of the wrist band, that the wrist band matches to the first patient, and based thereon allowing the healthcare provider to scan in medications for the first patient;
   while continually displaying, to the healthcare provider user via the display, the scan window that includes an image captured by the mobile electronic device and allows the healthcare provider user to scan a barcode of one or more medications by repeatedly positioning the mobile electronic device to align a barcode of a medication within the scan window,
      capturing, via the mobile electronic device, a barcode of a first medication,
      determining, based on the captured barcode of the first medication, that the first medication matches to a medication to be taken by the first patient, and based thereon temporarily displaying a pop-up match indication that subsequently dismisses without user intervention,
      capturing, via the mobile electronic device, a barcode of a second medication,
      determining, based on the captured barcode of the second medication, that there is a first issue with matching the second medication to a medication to be taken by the first patient, and based thereon temporarily displaying a pop-up issue indication that indicates the first issue and that subsequently dismisses without user intervention,
      capturing, via the mobile electronic device, a barcode of a third medication,
      determining, based on the captured barcode of the third medication, that the third medication matches to a medication to be taken by the first patient, and based thereon temporarily displaying a pop-up match indication that subsequently dismisses without user intervention;
   receiving, from the healthcare provider user via the interface, third user input corresponding to closing of the scan window, and based thereon displaying a medication list including at least the scanned first, second, and third medications and a respective status for each, including indications that the first and third medications match to a medication to be taken by the first patient and an indication of the first issue with matching the second medication to a medication to be taken by the first patient;
   receiving, from the healthcare provider user via the interface, fourth user input corresponding to selecting of one of the medications in the medication list, the selected medication being the second medication; and
   displaying, to the healthcare provider user, one or more interface elements configured to allow the user to address any outstanding action items for resolving the first issue associated with the selected second medication.

2. The mobile electronic device of claim 1, wherein the display comprises a touchscreen display.

3. The mobile electronic device of claim 1, wherein displaying, to the healthcare provider user, one or more interface elements configured to allow the user to address any outstanding action items for resolving the first issue associated with the selected second medication comprises displaying a list of actions that the user may take.

4. The mobile electronic device of claim 3, wherein the list of actions that the user may take includes an action allowing the user to add a comment regarding the selected second medication.

5. The mobile electronic device of claim 3, wherein the list of actions that the user may take includes an action allowing the user to mark the selected second medication as not given.

6. The mobile electronic device of claim 3, wherein the list of actions that the user may take includes an action allowing the user to discard the scan for the selected second medication.

7. The mobile electronic device of claim 3, wherein the list of actions that the user may take includes an action allowing the user to launch a task form.

8. A method for a mobile electronic device comprising a display and a computer readable medium storing a computer program for providing a medication administration workflow in a user-interface (UI), the computer program executable by at least one processor, the computer program comprising sets of instructions for facilitating the method, the method comprising:

displaying, to a healthcare provider user via the display, an interface of an electronic health record (EHR) software application comprising a listing of patients;

receiving, from the healthcare provider user via the interface, first user input corresponding to a selection of a first patient included in the listing of patients;

receiving, from the healthcare provider user via the interface, second user input corresponding to engagement with a scan button;

displaying, to the healthcare provider user via the display in response to the received second user input corresponding to engagement with the scan button, a scan window that includes an image captured by the mobile electronic device and allows the healthcare provider user to scan a wrist band of a patient by positioning the mobile electronic device to align the barcode of the wrist band within the scan window;

capturing, via the mobile electronic device, the barcode of the wrist band;

determining, based on the captured barcode of the wrist band, that the wrist band matches to the first patient, and based thereon allowing the healthcare provider to scan in medications for the first patient;

while continually displaying, to the healthcare provider user via the display, the scan window that includes an image captured by the mobile electronic device and allows the healthcare provider user to scan a barcode of one or more medications by repeatedly positioning the mobile electronic device to align a barcode of a medication within the scan window, capturing, via the mobile electronic device, a barcode of a first medication, determining, based on the captured barcode of the first medication, that the first medication matches to a medication to be taken by the first patient, and based thereon temporarily displaying a pop-up match indication that subsequently dismisses without user intervention, capturing, via the mobile electronic device, a barcode of a second medication, determining, based on the captured barcode of the second medication, that there is a first issue with matching the second medication to a medication to be taken by the first patient, and based thereon temporarily displaying a pop-up issue indication that indicates the first issue and that subsequently dismisses without user intervention, capturing, via the mobile electronic device, a barcode of a third medication, determining, based on the captured barcode of the third medication, that the third medication matches to a medication to be taken by the first patient, and based thereon temporarily displaying a pop-up match indication that subsequently dismisses without user intervention;

receiving, from the healthcare provider user via the interface, third user input corresponding to closing of the scan window, and based thereon displaying a medication list including at least the scanned first, second, and third medications and a respective status for each, including indications that the first and third medications match to a medication to be taken by the first patient and an indication of the first issue with matching the second medication to a medication to be taken by the first patient;

receiving, from the healthcare provider user via the interface, fourth user input corresponding to selecting of one of the medications in the medication list, the selected medication being the second medication; and displaying, to the healthcare provider user, one or more interface elements configured to allow the user to address any outstanding action items for resolving the first issue associated with the selected second medication.

9. The method of claim 8, wherein the display comprises a touchscreen display.

10. The method of claim 8, wherein displaying, to the healthcare provider user, one or more interface elements configured to allow the user to address any outstanding action items for resolving the first issue associated with the selected second medication comprises displaying a list of actions that the user may take.

11. The method of claim 10, wherein the list of actions that the user may take includes an action allowing the user to add a comment regarding the selected second medication.

12. The method of claim 10, wherein the list of actions that the user may take includes an action allowing the user to discard the scan for the selected second medication.

13. The method of claim 10, wherein the list of actions that the user may take includes an action allowing the user to launch a task form.

* * * * *